US005726020A

United States Patent [19]
Humphreys et al.

[11] Patent Number: 5,726,020
[45] Date of Patent: Mar. 10, 1998

[54] INHIBITION OF Ii SYNTHESIS

[75] Inventors: Robert E. Humphreys, Acton; Minzhen Xu, Northborough, both of Mass.

[73] Assignee: University of Massachusetts, Boston, Mass.

[21] Appl. No.: 661,627

[22] Filed: Jun. 11, 1996

[51] Int. Cl.$^6$ .......................... C12Q 1/68; G01N 33/53; C07H 21/00; C12N 5/00

[52] U.S. Cl. .......................... 435/6; 435/7.2; 435/7.21; 435/172.1; 435/320.1; 435/326; 536/24.5; 536/24.1

[58] Field of Search .......................... 435/6, 7.8, 172.1, 435/172.3, 320.1, 7.2, 7.21, 325, 326; 536/23.1, 23.5, 24.5, 24.1; 514/44

[56] References Cited

U.S. PATENT DOCUMENTS 5,585,479 12/1996 Hoke et al. .......................... 526/24.5

OTHER PUBLICATIONS

Gura, T. "Antisense Has Growing Pains", Science vol. 270: 575–577, Oct. 27, 1995.
Wu Pong, S. "Oligonucleotides: Opportunities for Drug Therapy Research", Pharmaceutical Technology, vol. 18: 102–114, Oct. 1994.
Stull, R. et al "Antigene, Ribozyme and Aptamer Nucleic Acid Drugs: Progress and Prospects", Pharmaceutical Research. vol. 12(4): 465–483, 1995.
Bennet, F. "Antisense Research", Science vol.271:434, Jan. 26, 1996.
Westermann, B. et al "Inhibition of Expression of SV40 virus large T–antigen byAntisense Oligonucleotides", Biomed. Biochim. Acta. vol. 48: 85–93, 1989.
Milligan, J. "Current Concepts in Antisense Drug Design", J. Medicinal Chemistry. vol. 36(14): 1923–1937, Jul. 9, 1993.
Miller, N. et al "Gene Transfer and Antisense Nucleic Acid Techniques", Parisitology Today. vol. 10(3): 92–97, 1994.
Rojanasakul, Y. "Antisense Oligonucleotide Therapeutics: Drug Delivery and Targeting", Advanced Drug Delivery Reviews. vol. 18: 115–131, 1996.
Weiss, R. "Upping the Antisense Ante", Science News, vol. 139: 108–109, 1991.
Stein, C. et al. "Antisense Oligonucleotides as Therapeutic Agents—Is the Bullet Really Magical?" Science vol. 261: 1004–1012, Aug. 20, 1993.
Wagner, R. "Gene Inhibition Using Antisense Oligonucleotides", Nature vol. 372: 333–335, Nov. 24, 1994.
Hatano, M. et al "Specific Inhibition of Class II MHC Gene Expression by Antisense RNA", International Immunology, vol. 1 (3): 260–266, 1989.
Clements, V. et al "Invariant Chain Alters The Malignant Phenotype of MHC Class II Tumor Cells", J. of Immunology, vol. 149(7): 2391–2396, Oct. 1, 1996.
Bertolino, P. et al "Correlation Between Invariant Chain Expression Level and Capability to Present Antigen to MHC class II–restricted T Cells" International Immunology vol. 3(5): 435–443, 1991.
James, W. "Towards Gene–Inhibition Therapy: A Review of Progress and Prospects in the Feild of Antiviral Antisense Nucleic Acids and Ribozymes" Antiviral Chemistry and Chemotherapy vol. 2(4) 191–214, 1991.
Clements et al., *J. Immunol.* 149: 2391–2396 (1992).
Baskar et al., *Cell. Immunol.* 155: 123–133 (1994).
Baskar et al., *J. Exp. Med.* 181: 619–629 (1995).
Singer et al., *EMBO J.* 3: 873–877 (1984).
Strubin, et al., *EMBO J.* 3: 869–872 (1984).
Miller and Germain, *J. Experi. Med.* 164: 1478–1489 (1986).
Héléne and Toulmé, *Biochimica et Biophysica Acta* 1049: 99–125 (1990).
Eguchi, *Annu. Rev. Biochem.* 60: 631–652 (1991).

*Primary Examiner*—George C. Elliott
*Assistant Examiner*—Sean McGarry
*Attorney, Agent, or Firm*—Kevin M. Farrell

[57] ABSTRACT

Disclosed are expressible reverse gene constructs, and oligonucleotides, which are characterized by the ability to hybridize with an Ii mRNA molecule, thereby inhibiting translation of the Ii mRNA molecule. These compositions are referred to generally as inhibitors of Ii expression. Also disclosed are MHC class II–positive antigen presenting cells containing an inhibitor of Ii expression. A particularly important class of MHC class II–positive antigen presenting cells are malignant MHC class II–positive antigen presenting cells (e.g., leukemia, lymphoma and melanoma). Also disclosed are methods which results in the display of an autodeterminant peptide, in association with an MHC class II protein, on the surface of an MHC class II–positive antigen presenting cell. In such methods, a specific inhibitor of Ii synthesis is introduced into an MHC class II–positive antigen presenting cell. The specific inhibitor functions, directly or indirectly, through the formation of a duplex molecule with mRNA encoding Ii. The formation of the duplex molecule functions to inhibit Ii synthesis at the translational level. Also disclosed are therapeutic methods for the treatment of malignancy in an MHC class II–positive antigen presenting cell, and autodeterminant peptides which are isolated from an MHC class II–positive antigen presenting cell.

23 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CGTTGGTCAT CCATGGCTCT AGCC　　　　　　　　　　　　　24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CACACATACC TTTCTGGCTC TC　　　　　　　　　　　　　22

( 2 ) INFORMATION FOR SEQ ID NO:3:

( i ) SEQUENCE CHARACTERISTICS:
        ( A ) LENGTH: 23 base pairs

-continued

```
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GCGCTGCTGC TGTGCAGAGC TGG                                                               23

( 2 ) INFORMATION FOR SEQ ID NO:4:

( i ) SEQUENCE CHARACTERISTICS:
        ( A ) LENGTH: 141 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TGCTGCTGCT GCTGCTGCTG CTGTGGGAAA AACTAGAGAT TAGAGCCATG GATGACCAAC        60

GCGACCTCAT CTCTAACCAT GAACAGTTGC CCATACTGGG CAACCGCCCT AGAGAGCCAG       120

AAAGGTGCAG CCGTGGAGCT C                                                 141
```

INHIBITION OF Ii SYNTHESIS

BACKGROUND OF THE INVENTION

The immune response to specific antigens is regulated by the recognition of peptide fragments of those antigens by T lymphocytes. Within an antigen presenting cell (APC), peptide fragments of the processed antigen become bound into the antigenic peptide binding site of major histocompatibility complex (MHC) molecules. These peptide-MHC complexes are then transported to the cell surface for recognition (of both the foreign peptide and the adjacent surface of the presenting MHC molecule) by T cell receptors on helper or cytotoxic T lymphocytes.

Two classes of MHC molecules have been identified. Class I MHC molecules receive peptides from endogenously synthesized proteins, such as an infectious virus, in the endoplasmic reticulum about the time of synthesis of the class I MHC molecules. The MHC class I complexed peptides are presented to CD8-positive cytotoxic T lymphocytes, which then become activated and can kill those virus-expressing cells directly. The antigenic peptide binding sites of MHC Class II molecules, however, are blocked around the time of synthesis by the invariant chain protein (Ii). Those MHC class II—Ii protein complexes are transported to a post-Golgi compartment where Ii is released by proteolysis and a specific antigenic peptide is bound to the MHC class II molecule. Those antigenic peptides are usually from exogenous antigens which have been internalized via either non-specific endocytosis or through interaction with a specific cell surface receptor on the antigen presenting cell. For example, surface immunoglobulin on B lymphocytes recognize intact protein antigens. Antigens are then internalized, digested and bound into the MHC class II molecules in the antigen presenting cells. Those antigenic peptide-MHC class II molecule complexes are reexpressed on the surface of the antigen presenting cells and recognized by CD4-positive helper T lymphocytes. Helper T lymphocytes then help cytotoxic T lymphocytes or B lymphocytes via physical contact and release of the cytokines.

The binding of antigenic peptides to MHC class II molecules is regulated in several ways by the invariant chain, which binds to MHC class II molecules at the time of their synthesis in the endoplasmic reticulum. Ii is released from MHC class II molecules in a post-Golgi compartment by proteolytic cleavage as a concerted step with exogenous antigenic peptide charging into the antigenic peptide binding site of the MHC class II molecules (Daibata et al., *Molecular Immunology* 31:255–260 (1994); Xu et al., *Molecular Immunology* 31:723–731 (1994)). The Ii protein prevents presentation of endogenous antigenic peptides which are derived in the cytoplasm and transported into the endoplasmic reticulum. These endogenously derived antigenic peptides cannot bind to MHC class II molecules since the Ii chain blocks the antigenic peptide binding site of MHC class II molecules until they reach a specific post-Golgi compartment where exogenous antigenic peptide charging occurs. In that compartment proteolytic digestion/release of Ii takes place in a concerted process with charging of the MHC class II molecule with the antigenic peptide from the specifically selected exogenous antigen.

Under normal conditions, endogenous peptides (with self determinants potentially leading to autoimmune disease) are not bound to MHC class II molecules since the Ii protein is always cosynthesized with nascent MHC class II molecules. Thus, no complexes with autodeterminant peptides (a peptide which is both synthesized and processed within the antigen presenting cell on the surface of which the peptide is ultimately presented) in MHC class II molecules are ever seen by the body's immune surveillance system. Tolerance is thus not developed to such determinants. If the expression of Ii protein is subsequently inhibited in certain cell types prone to autoimmune disease, such endogenous autodeterminants might then become presented by MHC class II molecules, initiating an autoimmune response to those endogenous antigens. By engineering such an effect in malignant cells, the resulting "autoimmune response" to endogenous tumor antigens is therapeutically useful in either restricting growth or eliminating those tumor cells.

The therapeutic effect of increased MHC class II expression has been demonstrated in MHC class II-negative cells (Clements et al., *Immunol.* 149:2391–2396 (1992); Baskar et al., *Cell. Immunol.* 155:123–133 (1994); and Baskar et al., *J. Exp. Med.* 181:619–629 (1995)). In those studies, transfection of genes for MHC class II molecules into a MHC class II-negative murine sarcoma generated MHC class II-positive, but Ii-negative tumor cell lines. Injection of these cells into a MHC compatible host led to the delayed growth of the parental tumors. Co-transfection of the gene for the Ii protein into a sarcoma cell line along with the MHC class II genes, inhibited the tumor-therapeutic effect of the MHC class II genes since the Ii chain blocked the presentation of endogenous tumor antigens.

SUMMARY OF THE INVENTION

In one aspect, the present invention relates to expressible reverse gene constructs, and oligonucleotides, which are characterized by the ability to hybridize with an Ii mRNA molecule, thereby inhibiting translation of the Ii mRNA molecule. These compositions are referred to generally as inhibitors of Ii expression. By acting against the mRNA for Ii these inhibitors decrease the expression of Ii protein up to about 90% in treated cells. Decreasing the expression of Ii permits the charging of MHC class II molecules with endogenous, T cell-presented antigenic determinants which would never have otherwise been seen by the immune system.

In another aspect, the present invention relates to MHC class II-positive antigen presenting cells containing an inhibitor of Ii expression. A particularly important class of MHC class II-positive antigen presenting cells are malignant MHC class II-positive antigen presenting cells (e.g., leukemia, lymphoma and melanoma).

The invention also relates to methods which results in the display of an autodeterminant peptide, in association with an MHC class II protein, on the surface of an MHC class II-positive antigen presenting cell. In such methods, a specific inhibitor of Ii synthesis is introduced into an MHC class II-positive antigen presenting cell. The specific inhibitor functions, directly or indirectly, through the formation of a duplex molecule with mRNA encoding Ii. The formation of the duplex molecule functions to inhibit Ii synthesis at the translational level.

Other aspects of the present invention include therapeutic methods for the treatment of malignancy in an MHC class II-positive antigen presenting cell, and autodeterminant peptides which are isolated from an MHC class II-positive antigen presenting cell.

DETAILED DESCRIPTION OF THE INVENTION

Figure 1:
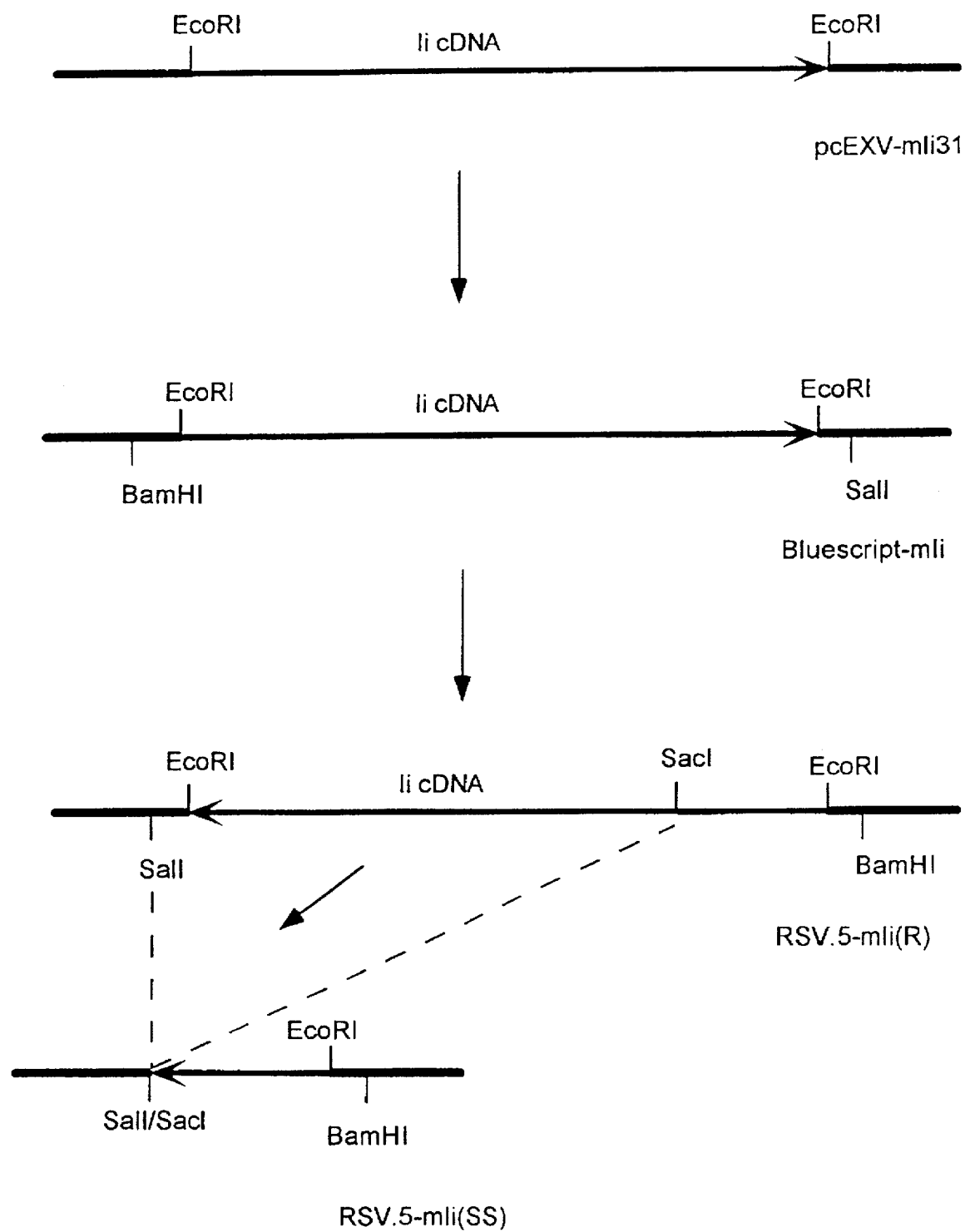
FIG. 1 is a diagrammatic representation of the cloning strategy employed in the construction of RSV.5-mIi(R) and RSV.5-mIi(SS).

The present invention is based on the discovery that Ii expression can be specifically and efficiently inhibited in a cell, and that such inhibition can be exploited in a therapeutic regimen. As discussed above, the antigenic peptide binding sites of MHC class II molecules are blocked at the time of MHC class II synthesis by Ii binding. The Class II MHC-Ii complexes are transported to a post-Golgi compartment where Ii is released by proteolysis and a specific antigenic peptide (usually from internalized exogenous antigens) is bound to the MHC class II molecule. Thus, the Ii protein prevents presentation of endogenous antigenic peptides which are derived in the cytoplasm and transported into the endoplasmic reticulum. Normally, these endogenously derived antigenic peptides cannot bind to MHC class II molecules since the Ii chain blocks the antigenic peptide binding site of MHC class II molecules until they are transported to a post-Golgi compartment.

As disclosed herein, by inhibiting Ii expression, it is now possible to charge MHC class II molecules with peptides from endogenously synthesized proteins. The ability to charge MHC class II molecules with antigenic peptides from endogenously synthesized proteins enables the targeting of unwanted cells in an individual (e.g., malignant cells) for destruction by an individual's own immune system.

The methods and compositions of the present invention are applicable to mammalian systems in general. cDNA encoding the Ii protein has been produced from mRNA isolated from a variety of mammalian systems and the nucleic acid sequence has been determined (Singer et al., *EMBO J.* 3: 873–877 (1984); Strubin, M. et al. *EMBO J.* 3:869–872 (1984); Henkes, W. et al., *Nucl. Acids Res.* 16: 11822 (1988)). The mammalian genes encoding Ii have been determined to be highly conserved. For example, the cDNA sequence encoding murine and human Ii have been determined to be approximately 85% homologous. The degree of conservation between the murine and rat sequences is greater than 90% (Henkes, W. et al., *Nucl. Acids Res.* 16:11822 (1988)).

In one aspect, the present invention relates to an expressible reverse gene construct. A reverse gene construct is an expressible DNA construct, the expression of which generates a mRNA molecule which is complementary to the mRNA molecule which encodes wild-type Ii. When coexpressed in an Ii producing cell, the mRNA product of the expressed reverse gene construct can hybridize to the mRNA encoding Ii thereby forming a duplex structure. The formation of this duplex structure has an inhibitory effect on the translation of the mRNA which encodes Ii. The net effect of this duplex formation is a reduction in Ii protein levels in the cell. Reduced levels of Ii in the cell enables MHC class II charging with antigenic peptides from endogenously synthesized antigens.

Preferably, the reverse gene construct is synthesized using cDNA encoding Ii from an organism corresponding to the cell type in which the reverse gene construct will be expressed. As indicated above, the human cDNA sequence which encodes Ii has been published. In light of the high degree of conservation among mammalian Ii genes, cDNA libraries from virtually any mammalian system of interest could be screened with an Ii probe (e.g., human or murine in origin) to isolate the corresponding Ii gene.

The selection of an expression vector background for use in the construction of the reverse gene construct is influenced by the cell type in which expression is desired. A great variety of appropriate vectors are available and one of skill in the art would be able to select an appropriate vector from among the many available without the necessity for undue experimentation. Similarly, regulatory signals required for efficient expression are selected based on the cell type in which expression is desired. The requirements for such regulatory signals are well known in the art, and unrestricted sources for such signals are generally known.

A reverse gene construct is produced by introducing an Ii cDNA fragment into an expression vector in reverse orientation, relative to the promoter, as compared to the wild-type orientation. In light of the fact that mRNA is known to assume a complex secondary structure which can interfere with its ability to hybridize to a complementary molecule, a full-length reverse gene construct (i.e., reverse gene construct which encodes a mRNA molecule which is complementary to the mRNA encoding Ii along its entire length) is not always the most efficient design. To develop more efficient constructs for Ii inhibition, it is often necessary to conduct routine experimentation in order to identify a less than full-length cDNA fragment which, when introduced into the reverse gene construct, is effective in inhibiting Ii synthesis.

In designing a less than full-length construct, it is often desirable to identify functionally significant regions of the mRNA encoding Ii, and design the reverse gene construct such that the mRNA encoded by the reverse gene construct is complementary with the functionally significant region. For example, functionally significant regions include regions involved in ribosome recognition of the mRNA, the translation initiation site, mRNA splice junctions and regions 3' of the translation termination codon which are required for polyadenylation.

In eukaryotic cells, the mechanism of initial ribosomal engagement with mRNA differs from the mechanism in prokaryotes. In eukaryotes, it is generally the 5'-most Met-specifying codons which are used as translation initiation points. The 5' end of eukaryotic mRNAs have a modified end comprising a methylated guanylate residue joined to the first unmodified nucleotide in a 5'-5' pyrophosphate linkage (often referred to as a 5' cap). Experiments have demonstrated, for example, that mRNAs lacking the 5' cap are not efficiently translated. Therefore, translation initiation in eukaryotes appears to involves recognition of the 5' cap followed by location of a consensus sequence surrounding the AUG codon. The consensus sequence for ribosomal recognition of a nearby protein coding sequence is "5'-ACCAUGG-".

The location of splice sites within primary transcripts can be determined by comparing the genomic DNA sequences (which encode the primary transcripts) with the corresponding cDNA sequence (produced from processed transcripts). Discontinuities identified in such a comparison mark intron/exon boundaries. Studies of such boundaries have revealed moderately conserved, short consensus sequences at the intron/exon boundaries and a tendency for a pyrimidine-rich region just upstream of the 3' splice site. In addition, universally conserved nucleotides are found at the first two (GU) and last two (AG) intron positions.

Polyadenylation requires the poly(A) signal, AAUAAA, and about 30 nucleotides downstream from the poly A addition site. Polyadenylation stabilizes the mRNA, thereby extending its half-life within the cell.

In the experiments described in the Exemplification section which follows, reverse gene constructs for the inhibition of Ii expression in murine cells were designed and tested.

The murine Ii protein is comprised of 215 amino acid residues (Singer et al., *EMBO J.* 3:873–877 (1984)). Thus, a full-length cDNA encoding this molecule is comprised of 645 base pairs of coding sequence.

In the Examples which follow, one full-length reverse gene construct, and one less than full-length reverse gene construct, were designed and tested. More specifically, the RSV.5-mIi(R) reverse gene construct contains an EcoR1 fragment from the murine mIi cDNA-containing plasmid pcEXV-mIi31 (Miller and Germain, *J. Experi. Med.* 164:1478–1489 (1986)). This construct contains the entire murine Ii cDNA coding sequence in reverse orientation. When expressed in murine A20 cells (Kim et al., *J. Immunol.* 122:549–554 (1979)), the full-length reverse gene construct RSV.5-mIi(R) was determined to inhibit Ii expression by 39.5% and 71.9% in the two trials conducted.

The less than full-length construct, RSV.5-mIi(SS) was generated by digesting RSV.5-mIi(R) with Sal1 and Sac1 to generate an Ii cDNA fragment containing 47 nucleotides of upstream 5' untranslated sequence, and the first 97 nucleotides of Ii coding sequence. When expressed in murine A20 cells, the less than full-length reverse gene construct RSV.5-mIi(SS) was determined to inhibit Ii expression by 89.3% and 95.3% in the two trials conducted.

As discussed previously, efficiency in the inhibition of expression of an endogenous protein using a reverse gene construct to inhibit translation is dependent, to a large extent on the secondary structure of the mRNA encoding the endogenous protein. The experiments described herein indicate that the Ii protein is particularly susceptible to inhibition of expression by a reverse gene construct. This conclusion is based on the fact that even a full-length reverse gene construct exhibited the ability to significantly inhibit Ii expression. Furthermore, the truncated version of the reverse gene construct produced even higher inhibition. This experimental work, together with the known high degree of conservation between mammalian Ii genes, can be considered to be a valid predictor of reverse gene construct activity in other mammalian systems, including human systems.

In addition to reverse gene constructs, oligonucleotides which hybridize specifically at or near functionally important regions of the Ii mRNA can be used to inhibit Ii expression at the translational level (see e.g., Hélène and Toulmé, *Biochimica et Biophsica Acta* 1049:99–125, (1990); and Eguchi, *Annu. Rev. Biochem.* 60: 631–652, (1991)). A variety of functionally significant regions of the Ii mRNA can be targeted in this manner.

For example, oligonucleotides complementary to the translation initiation site and/or upstream regions significant in connection with ribosome recognition can be used to inhibit translation. Similarly, oligonucleotides complementary to specific sequences of significance in connection with splicing and polyadenylation can be employed to inhibit Ii expression at the translation level.

As discussed in the Exemplification section which follows, A20 cells were incubated in a 96-well microplate ($10^5$ cells per well) in the presence of a mixture comprising the oligos disclosed in SEQ ID NOS: 1–3. At a 90 µM concentration of each oligonucleotide in the mixture, Ii expression was determined to be inhibited by about 66%. The oligonucleotide specified in SEQ ID NO: 1 is complementary to a region of the Ii mRNA thought to be important in connection with translation initiation. The oligonucleotide specified in SEQ ID NO: 2 is complementary to a region of the Ii mRNA thought to be important in connection with intron splicing. Finally, the oligonucleotide specified in SEQ ID NO: 3 is complementary to a region of the Ii mRNA thought to be important in connection with polyadenylation.

As discussed previously, the binding of antigenic peptides with MHC class II molecules is regulated in several ways by the invariant chain, which binds to MHC class II molecules at the time of their synthesis in the endoplasmic reticulum. Ii is released from MHC class II molecules in a post-Golgi compartment by proteolytic cleavage as a concerted step with exogenous antigenic peptide charging in the antigenic peptide binding site of the MHC class II molecules. The Ii protein prevents presentation of endogenous antigenic peptides which are derived in the cytoplasm and transported into the endoplasmic reticulum. These endogenously derived antigenic peptides cannot bind to MHC class II molecules since the Ii chain blocks the antigenic peptide binding site of MHC class II molecules until they reach a specific post-Golgi compartment where exogenous antigenic peptide charging occurs. In that compartment proteolytic digestion/release of Ii takes place in a concerted process with charging of the MHC class II molecule with the antigenic peptide from the specifically selected exogenous antigen (Daibata et al., *Molecular Immunology* 31:255–260 (1994); and Xu et al., *Molecular Immunology* 31:723–731 (1994)).

By inhibiting the expression of Ii in a cell of interest, endogenous autodeterminants can charge MHC class II molecules and become presented by the MHC class II molecules on the cell surface. This scenario results in the stimulation of an immune response to the endogenous autodeterminant peptide. Engineering this effect in malignant cells results in an "autoimmune response" to endogenous tumor antigens. Such a response is therapeutically useful in either restricting growth or eliminating the tumor cells.

A significant value of this method of therapy, in comparison with other methods which use antisense constructs for the therapy of disease, is that the transient or occasional use of the disclosed compositions leads to a priming of the immune system to the tumor-specific or tumor-related determinants. After such a priming event, the immune system, in the absence of additional antisense treatments is capable of rejecting the tumor. In contrast, in most current applications of antisense therapeutics for the control of disease (e.g., viral diseases such as HIV), upon discontinuation of the antisense therapeutic, the virus rebounds. As discussed, induction of an anti-tumor priming of the immune response can be pursued with in vivo or ex vivo application of antisense drugs.

In the experiments described below, malignant MHC class II-positive antigen presenting murine A20 cells, either containing or not containing a reverse gene construct of the type described above, were used to inoculate mice. Table 2 below shows percentage survival of the mice inoculated with the A20 cells. These experiments demonstrated that mice inoculated with A20 cells harboring the reverse gene construct RSV.5-mIi(SS) exhibited substantially greater rates of survivability than mice inoculated with A20 cells carrying no exogenous plasmid, or A20 cells carrying only the RSV.5 vector (conferring hygromycin resistance) but lacking an Ii insert.

Thus, in another aspect, the present invention relates to an MHC class II-positive cell containing an inhibitor of Ii synthesis. Such cells are useful, for example, in a therapeutic regimen in which an individual afflicted with a malignancy (e.g., leukemia, lymphoma or melanoma) is selected for treatment. Malignant MHC class II-positive antigen presenting cells are isolated from the individual. These procedures follow general protocols for immunotherapy (Clements et al., *Immunol.* 149:2391–2396 (1992); Baskar et al., *Cell. Immunol.* 155:123–133 (1994); Baskar et al., *J. Exp. Med.* 181:619–629 (1995); Hersey, *Drugs* 47:373 (1994); and Pardoll, *Immunol. Today* 14:310 (1993)). An inhibitor of Ii expression is introduced into the cells and the cells are cultured. As discussed above, such inhibitors include reverse gene constructs and antisense oligonucleotides. Since Ii is inhibited, endogenously produced antigen (including malignancy-specific antigens) are displayed on the surface of the cultured cells. The cultured cells are then reinfused into the individual afflicted with the malignancy. Preferably, prior to reinfusion, the cells are proliferation blocked (e.g., by radiation treatment). The reinfused cells stimulate the individual's own immune system to mount a response directed toward the malignant cells. By employing this strategy, the individual's immune system is stimulated to mount an autoimmune response directed specifically toward the malignant cells.

In addition to the use of malignant cells isolated from the individual to be treated, an inhibitor of Ii synthesis can also be introduced into an established malignant cell culture, or explants of fresh malignant tissue. Cells treated in this manner may also be useful in connection with a therapeutic method of the type described above.

In another aspect, the identification of Ii inhibitory products, and the specification of methods for their use to modify the expression of Ii protein, lead to new therapeutic and diagnostic procedures for the control of autoimmune diseases. A specific example is the use of the products and methods of this invention to identify autoimmune disease-related autodeterminants. Ii-antisense treatment of MHC class II-positive cells leads to the binding of an enlarged repertoire and/or enhanced quantities of autodeterminants to MHC class II molecules. Those T cell-presented, disease inducing peptides can be eluted from immunopurified MHC class II molecules from cells in which the Ii-expression has been inhibited, for example, using the compositions described above. Discovery of those autodeterminants (some of which are tumor-specific determinants) is the first step in the development of disease-specific immunotherapeutics. Given such autodeterminant peptides, it is a matter of routine experimentation to develop new therapeutic methods.

In another aspect, the present invention relates to enhancement of endogenous antigen presentation which can lead to the elimination of undesirable cells in an individual. This aspect of the invention can be applied to the elimination of any cell characterized by the presence of non-native intracellular proteins which are antigenically distinguishable from native intracellular proteins. As discussed previously, malignant cells fall within this class since they contain, for example, oncogene products which are antigenically distinguishable from their native cellular counterparts. In addition to the malignant cells discussed above, other non-malignant cells (e.g., virus-infected cells) can be eliminated through inhibition of Ii expression. In this embodiment, ex vivo therapy with an inhibitor of Ii synthesis can be employed. Alternatively, expression vectors suitable for tissue-specific expression in an individual may be useful for the introduction of a reverse gene construct into the cells of an individual. Tissue specific regulatory signals can provide the refinement of expression necessary for such a therapeutic method.

For example, virally infected cells treated with the Ii antisense construct can have enhanced MHC class II presentation of viral determinants leading to the destruction of those infected cells and/or to an expansion of helper T lymphocytes which regulate the immunoglobulin-mediated response to the viral infection. In this regard, only a portion of the virally infected cells need be treated ex vivo with the Ii antisense construct and reinfused into the patient. Particularly in the case of Epstein-Barr virus infection of normal B cells, in which Ii has been demonstrated to be greatly overexpressed in part to suppress anti-EBV immune response, would such treatment be effective in enhancing an anti-EBV immune response. Likewise in the case of HIV-infected CD4+ T lymphocytes which can upon activation express MHC class II antigens, might an anti-HIV immune response be enhanced by treatment of those cells with an anti-Ii construct.

The present invention also finds application in the treatment of a pathogenic autoimmune response. More specifically, enhancement of endogenous antigen presentation during certain phases of an autoimmune disease cycle is stimulated in order to down regulate a pathogenic autoimmune response. It has been demonstrated, for example, in certain animal models of arthritis (e.g., rat adjuvant arthritis) that, after an initial phase of aggressive development of disease, suppressor T lymphocytes, directed against the same antigenic determinants which initiated the pathogenic process, will then suppress those immune responses. During that second phase of down regulation of the disease process (clinically seen as an indicator of remission), enhancement of presentation of endogenous autoantigens in cells contacted with the Ii-antisense construct will down regulate the disease. Furthermore, Ii antisense construct treatment of cells lacking co-stimulatory signals, (e.g., cells without B7, or in which B7 expression is suppressed by treatment with B7 antisense constructs), will lead to anergic responses.

In practice, a population of cells (e.g., lymphocytes) is first isolated from the individual using standard techniques. The population of cells is then treated with an inhibitor of Ii synthesis ex vivo, as discussed previously. The individual is then monitored for signs of remission. When indications of remission are observed (as determined by predefined clinical signs and symptoms) the cells treated with the inhibitor of Ii synthesis are reinfused into the individual.

In another aspect of the present invention, increased expression of Ii protein by genetic insertion of the Ii gene under the control of tissue specific promoters can be applied to the suppression of an autoimmune disease involving those tissues. Vectors appropriate for the introduction of Ii into the cells of an individual are characterized in the literature. For example, insertion of the Ii gene under the control of the insulin promoter will lead to enhanced expression of Ii in beta cells which are destroyed in diabetes mellitus. In addition, insertion of the Ii gene under the control of the thyroglobulin promoter will lead to enhanced expression of Ii in thyroid follicular cells which are destroyed in some forms of thyroiditis. The mechanism of such constructs in the prevention of autoimmune disease is thought to follow from increased constitutive expression of Ii during a cellular activating event, for example a viral infection, in which increased expression of MHC class II alpha and beta chains might be found without concomitant increased expression of the Ii protein. Without "protection" of the MHC class II antigenic binding site by Ii protein, enhanced presentation of autoantigens occurs. This therapeutic concept is a conceptual mirror image of the application of an Ii-antisense construct in order to enhance presentation of autodeterminants.

EXAMPLES

Example 1

Design and Synthesis of Reverse Gene Constructs

As shown in FIG. 1, the murine Ii (mIi) gene-containing plasmid pcEXV-mIi31 (Miller and Germain, *J. Experi. Med.*

164: 1478–1489 (1986)) was digested with the restriction endonuclease Eco RI to release the mIi gene. Following purification, the mIi gene was cloned into the Eco RI site of the Bluescript vector (Stratagene). The orientation of the mIi gene was determined by analysis of the pattern of its digestion with the Bgl I restriction endonuclease. The Bluescript-mIi construct containing mIi gene oriented with the direction of transcription towards the Sal I shown in FIG. 1 was selected.

The Bluescript-mIi construct was then digested with the restriction endonucleases Sal I and Bam HI to release a fragment containing the mIi gene. This fragment was subcloned into the RSV.5 expression vector (Long, Hum. Immunol. 31:229–235 (1991)) which had been digested with Sal I and Bam HI endonucleases. The RSV.5 vector also contained a hygromycin resistance gene and could therefore be selected with hygromycin. The resulting RSV.5-mIi antisense construct containing the reversed entire mIi gene was designated RSV.5-mIi(R).

The RSV.5-mIi(R) construct was further digested with the restriction endonucleases Sal I and Sac I. Digestion with these enzymes generates an Ii encoding fragment comprising 47 nucleotides from the 5' untranslated region, and the first 94 nucleotides of coding sequence. Following purification of the large fragment by gel electrophoresis, the Ii fragment was treated with the Klenow DNA polymerase I to fill the Sal I and Sac I ends, thereby creating blunt ends. The blunt ends were ligated with T4 DNA ligase. The resulting mIi antisense plasmid, containing the first 94 nucleotides of Ii structural gene and 47 nucleotides of upstream sequence in reversed orientation, was named RSV.5-mIi(SS).

The strategy for the construction of RSV.5-mIi(R) and RSV.5-mIi(SS) is diagramed in FIG. 1. The antisense plasmid constructs of RSV.5-mIi(R) and RSV.5-mIi(SS), driven by the promoter of Rous Sarcoma Virus long terminal repeat (LTR), can transcribe the antisense RNA which is complementary, and thus hybridizes, to Ii mRNA in order to inactivate the Ii mRNA. The sequence of the Ii cDNA insert of RSV.5-mIi(SS) is presented in SEQ ID NO: 4.

Example 2

Generation of Transfected Cell Lines

A20 cells (Kim et al., J. Immunol. 122:549–554 (1979)) ($15 \times 10^6$) were washed twice with prewarmed RPMI-1640 medium (Gibco) without serum and resuspended in 0.5 ml of RPMI-1640 medium. 15 µg of plasmid DNA (either RSV.5-mIi(R) or RSV.5-mIi(SS)) was mixed with the cell suspension. This mixture was subjected to electroporation with an electroporator at 300V, 625 µF per 0.5 ml. The cell suspension was incubated at room temperature for 10 minutes. The cells were then diluted in 10 ml of RPMI-1640 medium with 10% fetal bovine serum and cultured in 24-well microtiter plates for 24 hours. The antibiotic hygromycin (800 µg per ml) was then added for selection. The RPMI-1640 medium containing 800 µg per ml of hygromycin was changed every two days until colonies were visible. Suppression of the expression of Ii protein was examined by intracellular staining with an anti-mouse Ii monoclonal antibody, In.1 (Koch, N. et al., Nature 299:644–645 (1982)). In this assay, the cells were smeared on a microscope slide, air-dried, fixed in acetone and incubated with the rat anti-mouse Ii monoclonal antibody for 40 min. The slides were washed with sodium phosphate-buffered saline solution twice and incubated with fluorescein isothiocyanate-labeled goat anti-rat Ig(H,L) antibody.

Example 3

Expression of Ii in Transfected Cells

Expression of the Ii protein in A20 cells (A20), A20 cells stably transfected with RSV.5-mIi(R) (A20(R)), and A20 cells stably transfected with RSV.5-mIi(SS) (A20(SS)) was quantitated by intracellular immunofluorescence staining for the endogenous Ii protein identified with the In.1 monoclonal antibody. The slides of stained cells were then examined by quantitative fluorescent image scanning microscopy. Each test slide was accompanied by a slide from a well of A20 cells as a positive control. Inhibition of Ii expression in cells harboring a reverse gene construct was observed. The inhibition of Ii expression in reverse gene construct carrying cell lines was expressed as a percentage of the positive control. Stable transfection with RSV.5-Ii(R) plasmid resulted in a 39.5% and 71.9% inhibition of Ii synthesis in two trials as shown in Table 1. In two trials with the RSV.5-Ii(SS) plasmid, a 89.3% and 95.3% suppression of Ii protein expression was observed as shown in Table 1. As also shown in Table 1, this effect was observed without significant effect on the expression of the MHC class II proteins. In this table, (R1) and (R2), (SS1) and (SS2) are individual cell lines from transfections with the RSV.5-mIi (R) and RSV.5-mIi(SS) plasmids, respectively.

TABLE 1

| Expression of Ii in A20, A20(R), and A20(SS) | | |
|---|---|---|
| Cell line | MHC Class II Expression | Ii Expression |
| A20 | 100 | 100 |
| A20(R1) | 96 | 60.5 |
| A20(R2) | 99 | 28.1 |
| A20(SS1) | 84 | 10.7 |
| A20(SS2) | 92 | 4.7 |

Example 4

Survival of Mice Inoculated with Transfected Cells

Mice were primed with 0.5 ml pristane/mouse one week before tumor cell inoculations. Each mouse was injected intraperitoneally with $3 \times 10^6$ of the following: A20 cells (harboring no plasmid) (designated A20 in Table 2), or A20(hygro)cells (containing RSV.5 plasmid only) (designated A20(hygro) in Table 2), or A20 cells harboring RSV.5-mIi(SS) plasmid (designated "A20(SS)" in Table 2). The survival of mice inoculated with each of the three types of cell lines was determined. The survival of mice inoculated with A20 cells was not significantly different from mice receiving A20(hygro) cells. Mice receiving A20 cells harboring RSV.5-mIi(SS) plasmid survived significantly longer than the mice inoculated with either A20 cells of A20 cells stably transfected with the hygromycin-resistant plasmid (Table 2). For example, at day 22, 100% of the mice receiving A20 cells harboring RSV.5-mIi(SS) plasmid survived, compared with only 40% survival observed for mice receiving A20 cells alone, or A20 cells containing the RSV.5 plasmid alone.

TABLE 2

Percentage survival of mice receiving A20 cells with or without Ii antisense treatment.

| Days | Cell Lines | | |
|---|---|---|---|
| | A20 | A20(hygro) | A20(SS) |
| 2 | 100 | 100 | 100 |
| 4 | 100 | 100 | 100 |
| 6 | 100 | 100 | 100 |
| 8 | 100 | 100 | 100 |
| 10 | 80 | 80 | 100 |
| 12 | 80 | 80 | 100 |
| 14 | 40 | 40 | 100 |
| 16 | 40 | 40 | 100 |
| 18 | 40 | 40 | 100 |
| 20 | 40 | 40 | 100 |
| 22 | 40 | 40 | 100 |
| 24 | 40 | 40 | 80 |
| 26 | 20 | 20 | 60 |
| 28 | 20 | 20 | 60 |
| 30 | 0 | 20 | 40 |
| 32 | 0 | 20 | 40 |
| 34 | 0 | 20 | 40 |
| 36 | 0 | 20 | 40 |
| 38 | 0 | 20 | 40 |
| 40 | 0 | 20 | 20 |

Example 5

Inhibition of Ii Expression with Antisense Oligonucleotides

A20 cells ($10^5$) were incubated in the 96-well microplate for 2.5 hours at 37° C. in 100 µl of medium in the presence of a mixture of oligo 1 (SEQ ID NO: 1), 2 (SEQ ID NO: 2), and 3 (SEQ ID NO: 3). More specifically, three mixtures of the oligonucleotides were tested, comprising 10, 30 or 90 µM of each oligonucleotide. As mentioned previously: the oligonucleotide specified in SEQ ID NO: 1 is complementary to a region of the Ii mRNA thought to be important in connection with translation initiation; the oligonucleotide specified in SEQ ID NO: 2 is complementary to a region of the Ii mRNA thought to be important in connection with intron splicing; and the oligonucleotide specified in SEQ ID NO: 3 is complementary to a region of the Ii mRNA thought to be important in connection with polyadenylation.

The medium was removed and 100 µl labeling medium (no methionine) and 50 µCi of [$^{35}$S]methionine was added in the presence of the same concentration of oligos 1, 2, and 3 for another 2.5 hours. The cells were harvested and washed with phosphate buffer saline solution and lysed. The cell lysates were immunoprecipitated with anti-mouse Ii monoclonal antibody, In.1. The radioactivity of immunoprecipitates was counted.. At the concentration of 90 µM of each of the oligos 1, 2, and 3, Ii expression was inhibited by about 66% as determined by radioactivity counting. The 10 µM and 30 µM mixture concentrations had no effect. The use of individual oligonucleotides at the concentrations tested also had no observed effect.

---

We claim:

1. An expressible reverse gene construct, comprising a DNA molecule which encodes a first mRNA molecule which is complementary to a second mRNA molecule which encodes a mammalian Ii protein, the first mRNA molecule having the ability to hybridize with the second mRNA molecule thereby inhibiting translation of the second mRNA molecule, the first mRNA molecule being complementary with a portion of the second mRNA molecule comprising the translation initiation site through at least a portion of the second exon.

2. The expressible reverse gene construct of claim 1 wherein the DNA molecule is a cDNA molecule.

3. The expressible reverse gene construct of claim 2 wherein the first mRNA molecule is complementary with the second mRNA molecule along the entire length of the Ii coding sequence.

4. The expressible reverse gene construct of claim 1 wherein the DNA sequence which encodes the first mRNA molecule comprises SEQ ID NO: 4.

5. An oligonucleotide which is complementary to a mRNA molecule encoding mammalian Ii, the oligonucleotide having the sequence of SEQ ID NO: 1.

6. An MHC class II-positive antigen presenting cell containing an expressible reverse gene construct, the expressible reverse gene construct comprising a DNA molecule which encodes a first mRNA molecule which is complementary to a second mRNA molecule which encodes a mammalian Ii protein, the first mRNA molecule having the ability to hybridize with the second mRNA molecule, thereby inhibiting translation of the second mRNA molecule, the first mRNA being complementary with a portion of the second mRNA molecule comprising the translation initiation site through at least a portion of the second exon.

7. The MHC class II-positive cell of claim 6 wherein the class II-positive cell is a malignant cell.

8. The MHC class II-positive cell of claim 7 wherein the malignancy is selected from the group consisting of the leukemia, lymphoma and melanoma classes.

9. The MHC class II-positive cell of claim 7 wherein an antigenic tumor-associated peptide is displayed on the cell surface in association with an MHC class II protein.

10. The MHC class II-positive antigen presenting cell of claim 6 wherein the DNA molecule is a cDNA molecule.

11. The MHC class II-positive antigen presenting cell of claim 6 wherein the first mRNA molecule is complementary with the second mRNA molecule along the entire length of the Ii coding sequence.

12. The MHC class II-positive antigen presenting cell of claim 6 wherein the first mRNA molecule is complementary to a portion of the second mRNA molecule, the portion comprising less than the entire length of the Ii coding sequence.

13. The MHC class II-positive antigen presenting cell of claim 6 wherein the DNA molecule which encodes the first mRNA molecule comprises the DNA molecule of SEQ ID NO: 4.

14. A method which results in the display of an autodeterminant peptide, in association with an MHC class II protein, on the surface of an MHC class II-positive antigen presenting cell, the method comprising:

a) providing the MHC class II-positive antigen presenting cell; and b) introducing into the MHC class II-positive antigen presenting cell, the oligonucleotides of SEQ ID NOS: 1, 2 and 3.

15. A method which results in the display of an auto determinant peptide, in association with an MHC class II protein, on the surface of an MHC class II-positive antigen presenting cell, the method comprising:

a) providing the MHC class II-positive antigen presenting cell; and b) introducing into the MHC class II-positive antigen presenting cell, an expressible reverse gene construct, the expressible reverse gene construct, the expressible reverse gene construct comprising a DNA molecule which encodes a first mRNA molecule which is complementary to a second mRNA molecule which encodes a mammalian Ii protein, the first mRNA molecule having the ability to hybridize with the second mRNA molecule, thereby inhibiting translation of the second mRNA molecule, the first mRNA being complementary with a portion of the second mRNA molecule comprising the translation initiation site through at least a portion of the second exon.

16. The method of claim 15 wherein the DNA molecule is a cDNA molecule.

17. The method of claim 15 wherein the first mRNA molecule is complementary with the second mRNA molecule along the entire length of the Ii coding sequence.

18. The method of claim 15 wherein the first mRNA molecule is complementary to a portion of the second mRNA molecule, the portion comprising less than the entire length of the Ii coding sequence.

19. The method of claim 15 wherein the DNA molecule which encodes the first mRNA molecule comprises the DNA molecule of SEQ ID NO: 4.

20. An oligonucleotide which is complementary to a mRNA molecule encoding mammalian Ii, the oligonucleotide having the sequence of SEQ ID NO: 2.

21. An oligonucleotide which is complementary to a mRNA molecule encoding mammalian Ii, the oligonucleotide having the sequence of SEQ ID NO: 3.

22. An MHC class II-positive antigen presenting cell containing oligonucleotides having the nucleotide sequences shown in SEQ ID NOS: 1, 2 and 3.

23. A method for isolating an autodeterminant peptide, comprising:

a) providing a MHC class II-positive antigen presenting cell;

b) introducing into the MHC class II-positive antigen presenting cell an expressible reverse gene construct, the expressible reverse gene construct comprising a DNA molecule which encodes a first mRNA molecule which is complementary to a second mRNA molecule which encodes a mammalian Ii protein, the first mRNA molecule having the ability to hybridize with the second mRNA molecule, thereby inhibiting translation of the second mRNA molecule, the first mRNA being complementary with a portion of the second mRNA molecule comprising the translation initiation site through at least a portion of the second exon;

c) solubilizing the MHC class II-positive antigen presenting cell of step b);

d) immunopurifying the MHC class II molecules; and e) eluting autodeterminant peptides from the MHC class II molecules of step d) by acid treatment.

* * * * *